(12) United States Patent
Redmond et al.

(10) Patent No.: US 8,535,374 B2
(45) Date of Patent: Sep. 17, 2013

(54) ANNULOPLASTY DEVICE FOR TRICUSPID VALVE REPAIR

(75) Inventors: Jerald Redmond, Blaine, MN (US); Timothy R. Ryan, Shorewood, MN (US); Jason L. Quill, Minneapolis, MN (US); Alexander J. Hill, Blaine, MN (US); Michael A. Gloss, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 625 days.

(21) Appl. No.: 12/011,482

(22) Filed: Jan. 25, 2008

(65) Prior Publication Data

US 2009/0036979 A1 Feb. 5, 2009

Related U.S. Application Data

(60) Provisional application No. 60/897,696, filed on Jan. 26, 2007.

(51) Int. Cl.
*A61F 2/24* (2006.01)

(52) U.S. Cl.
USPC .......................................... 623/2.36; 623/2.37

(58) Field of Classification Search
USPC ............................................... 623/2.36–2.37
See application file for complete search history.

(56) References Cited

U.S. PATENT DOCUMENTS

| | | | |
|---|---|---|---|
| 5,104,407 A | 4/1992 | Lam et al. | |
| 5,824,066 A | 10/1998 | Gross | |
| 6,749,630 B2 | 6/2004 | McCarthy et al. | |
| 6,786,924 B2 | 9/2004 | Ryan et al. | |
| 6,805,710 B2 | 10/2004 | Bolling et al. | |
| 6,858,039 B2 | 2/2005 | McCarthy | |
| 6,908,482 B2 | 6/2005 | McCarthy et al. | |
| 2001/0049557 A1* | 12/2001 | Chinn et al. | 623/2.36 |
| 2003/0093148 A1* | 5/2003 | Bolling et al. | 623/2.36 |
| 2003/0208264 A1 | 11/2003 | McCarthy et al. | |

(Continued)

FOREIGN PATENT DOCUMENTS

| EP | 1 034 753 | 9/2000 |
|---|---|---|
| WO | 00/74603 | 12/2000 |

(Continued)

OTHER PUBLICATIONS

Carpentier et al., "Surgical management of acquired tricuspid valve disease," Journal of Thoracic Cardiovascular Surgeon, 67(1):53-65 (1974).

(Continued)

*Primary Examiner* — Thomas J Sweet
*Assistant Examiner* — Tiffany Shipmon

(57) ABSTRACT

Annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first and second ends; wherein the ring body is curvilinear, with substantially no flat portions, forming a shape, and the ends are configured such that when the device is implanted, the first end will be located near the junction of the septal and anterior aspects of the annulus and the second end will be located near the septal aspect of the annulus. Related methods.

16 Claims, 11 Drawing Sheets

(56) References Cited

U.S. PATENT DOCUMENTS

| | | | |
|---|---|---|---|
| 2005/0004669 A1 | 1/2005 | Sievers | |
| 2005/0021135 A1 | 1/2005 | Ryan | |
| 2005/0043791 A1 | 2/2005 | McCarthy et al. | |
| 2005/0256568 A1* | 11/2005 | Lim et al. | 623/2.36 |
| 2005/0288776 A1* | 12/2005 | Shaoulian et al. | 623/2.37 |
| 2006/0025856 A1 | 2/2006 | Ryan et al. | |
| 2006/0129236 A1 | 6/2006 | McCarthy | |
| 2008/0275551 A1* | 11/2008 | Alfieri | 623/2.36 |

FOREIGN PATENT DOCUMENTS

| | | |
|---|---|---|
| WO | WO 00/74603 | 12/2000 |
| WO | WO 03/020178 | 3/2003 |
| WO | 2005/112830 | 12/2005 |
| WO | 2006/102513 | 9/2006 |

OTHER PUBLICATIONS

Sharony et al., "Repair of Tricuspid Regurgitation: The Posterior Annuloplasty Technique," Operative Techniques in Thoracic and Cardiovascular Surgery, Nov.; 8(4):177-183 (2003).

Minale et al., "New Developments for Reconstruction of the Tricuspid Valve," J. Thorac. Cardiovas. Surg., Oct.; 94(4):626-31 (1987).

Antunes et al., "DeVega Annuloplasty of the Tricuspid Valve," Operative Techniques in Thoracic and Cardiovascular Surgery, Nov.; 8(4):169-176 (2003).

Fukuda et al., "Three Dimensional Geometry of the Tricuspid Annulus in Healthy Subjects and in Patients with Functional Tricuspid Regurgitation: A Real-Time, 3-Dimensional Echocardiographic Study," Circulation, 114 (I Suppl) I492-8 (2006).

Ton-Nu et al., "Geometric Determinants of Functional Tricuspid Regurgitation: Insights From 3-Dimensional Echocardiography," Circulation, 114:143-149 (2006).

Hiro et al., "Sonometric Study of the Normal Tricuspid Valve Annulus in Sheep," The Journal of Heart Valve Disease, 13(3):452-460 (2004).

Ton-Nu, et al, "Geometric Determinants of Functional Tricuspid Regurgitation," Circulation, Journal of the American Heart Association, (2006), pp. 143-149.

Fukuda, et al, "Three-Dimensional Geometry of the Tricuspid Annulus in Healthy Subjects and in Patients With Functional Tricuspid Regurgitation," Circulation, Journal of the American Heart Association, (2006), pp. I-492-I-498.

Carpentier-Edwards Classic Annuloplasty Rings, Edwards Lifesciences, (2003), 2 pgs.

Carpentier-Edwards Physio Annuloplasty Ring, Edwards Lifesciences, (2003), 2 pgs.

Hiro, et al, "Sonometric Study of the Normal Tricuspid Valve Annulus in Sheep," J. Heart Valve Dis., vol. 13, No. 1, Jan. 2004, pp. 452-460.

Filsoufi, et al., "Surgical Management of Functional Tricuspid Regurgitation with a New Remodeling Annuloplasty Ring," Mount Sinai Journal of Medicine, vol. 73, No. 6, Oct. 2006, pp. 874-879.

McGuire, et al., "Dimensions of the Triangle of Koch in Humans," The American Journal of Cardiology, vol. 70, Sep. 15, 1992, pp. 829-830.

Raffoul, et al, "Clinical Evaluation of the Physio Annuloplasty Ring," CHEST, 1998; 113; 1296-1301.

Timek, et al., "Annular Height-to-Commissural Width Ratio of Annuloplasty Rings In Vivo," Circulation, Aug. 30, 2005, pp. I-423-I-428.

Salgo, et al., "Effect of Annular shape on Leaflet Curvature in Reducing Mitral Leaflet Stress," Circulation, Aug. 6, 2002, pp. 711-717.

Gorman, et al., "The Effect of Regional Ischemia on Mitral Valve Annular Saddle Shape," Society of Thoracic Surgeons, 2004;77:544-8.

Sharony, et al., "Repair of Tricuspid Regurgitation: the Posterior Annuloplasty Technique," Operative Techniques in Thoracic and Cardiovascular Surgery, vol. 8, No. 4, Nov. 2003, pp. 177-183.

Manuel J. Antunes, "DeVega Annuloplasty of the Tricuspid Valve," Operative Techniques in Thoracic and Cardiovascular Surgery, vol. 8, No. 4, Nov. 2003, pp. 169-176.

Carpentier et al., "Surgical management of acquired tricuspid valve disease," J. Thorac. Cardiovasc. Surg., 1974; 67(1): 53-65.

Minale et al., "New Developments for Reconstruction of the Tricuspid Valve," J. Thorac. Cardiovasc. Surg., Oct. 1987; 94(4): 626-31.

\* cited by examiner

ANNULOPLASTY DEVICE FOR TRICUSPID VALVE REPAIR

PRIORITY

The present non-provisional patent application claims benefit from U.S. Provisional Patent Application having Ser. No. 60/897,696, filed on Jan. 26, 2007, by Redmond et al., and titled ANNULOPLASTY RING FOR TRICUSPID VALVE REPAIR, wherein the entirety of said provisional patent application is incorporated herein by reference.

TECHNICAL FIELD

The present invention relates generally to devices and methods for repair of heart valves, and more particularly to an annuloplasty device having two-dimensional (2D) and/or three-dimensional (3D) shape that either mimics a healthy, native tricuspid valve annulus in shape or otherwise restores the annular shape of an incompetent tricuspid valve annulus to a shape more closely representing the 3D shape of a healthy, native tricuspid valve.

BACKGROUND OF THE INVENTION

Heart valve disease is a widespread condition in which one or more of the valves of the heart fails to function properly. Various surgical techniques may be used to replace or repair a diseased or damaged valve. In just one way, in a valve replacement surgery, damaged leaflets of the valve are excised and the annulus is sculpted to receive a replacement valve. Another less drastic method for treating defective valves is repair or reconstruction by annuloplasty, in which the effective size of the valve annulus is contracted and reinforced, by attaching a prosthetic annuloplasty repair segment or ring to an interior wall of the heart around the valve annulus. The annuloplasty ring is designed to support the functional changes that occur during the cardiac cycle; maintaining coaptation and valve integrity.

One of the two atrio-ventricular valves in the heart is the tricuspid valve. The tricuspid valve regulates blood flow between the right atrium and the right ventricle. Anatomically speaking, the tricuspid valve 10, as seen in FIG. 1, includes an annulus 12 that is the portion of the wall of the heart where three valve leaflets 14, 16, 18 (septal, anterior, and posterior, respectively) insert into the heart wall tissue. The leaflets 14, 16, 18 extend inward into the valve or flow orifice defined by the annulus 12. There are three commissures between the three leaflets, which include an anteroseptal commissure 20, a posteroseptal commissure 22 and an anteroposterior commissure 24. Chordae tendinae 26 connect the leaflets to papillary muscles located in the right ventricle to control the movement of the leaflets. The tricuspid annulus 12 is an ovoid-shaped structure ring at the base of the valve. The annulus 12 has contractile function and can change shape throughout a cardiac cycle. The portions of the tricuspid valve annulus 12 that are attached to the septal 14, anterior 16 and posterior 18 leaflets are called the septal 34, anterior 36 and posterior 38 aspects, respectively. The anterior and posterior leaflets are also known, respectively, as the anterosuperior and inferior leaflets. Similarly, the aspects of the annulus may be referred to using these alternative terms.

With particular regard to the tricuspid valve, the primary dysfunction is dilation of the anterior and posterior aspects of the valve annulus. Annulus dilation can lead to incomplete leaflet coaptation, causing a condition known as tricuspid regurgitation. Studies have shown that the posterior aspect can be dilated as much as 80% of its original length, whereas the anterior aspect can be dilated by as much as 40% (Carpentier et al. (1974), Surgical management of acquired tricuspid valve disease, *Journal of the Thoracic Cardiovascular Surgeon*, 67(1): 53-65). The septal aspect of the annulus lies along the atrioventricular septum of the heart and does not dilate as much as the other aspects (typically 10% or less of its original length).

Consequently, when a tricuspid valve is repaired surgically, the goal is to reduce the size of and reinforce one or both of the anterior and posterior aspects of the valve annulus. Early methods used to reduce the size of the anterior and/or posterior aspects were suture-based. One method called "bicuspidization" used sutures to effectively eliminate the posterior leaflet, and is described in Sharony et al. (2003), Repair of Tricuspid Regurgitation The Posterior Annuloplasty Technique, *Operative Techniques in Thoracic and Cardiovascular Surgery*, November; 8(4): 177-183. Another method called "sliding plasty" involves separation of the leaflets from the annulus, plication/shortening of the annulus, and reattachments of the leaflets, and is described in Minale et al. (1987), New Developments for Reconstruction of the Tricuspid Valve, *J. Thorac. Cardiovasc. Surg.*, October; 94(4): 626-31. Yet another method used, called the "modified DeVega tricuspid annuloplasty," involves placing a suture or series of sutures around the annulus and pulling the sutures tight to reduce the perimeter of the annulus, as described in Antunes et al. (2003), DeVega Annuloplasty of the Tricuspid Valve, *Operative Techniques in Thoracic and Cardiovascular Surgery*, November; 8(4): 169-176.

One current method used to reduce the tricuspid valve annulus is remodeling annuloplasty. Remodeling annuloplasty involves implanting a prosthetic ring or band in a supra annular position. The purpose of the ring or band is to restrict and/or support an annulus to correct and/or prevent valvular insufficiency. Remodeling annuloplasty is an important part of surgical valve repair. Three objectives of surgical valve repair include: 1) restore large surface of leaflet coaptation; 2) preserve leaflet mobility; and 3) stabilize the annulus and avoid further dilatation. In remodeling annuloplasty, both annuloplasty rings and annuloplasty bands are used for repair of valves. In general terms, annuloplasty rings completely encompass a valve annulus, while annuloplasty bands are designed to primarily encompass only a portion of the valve annulus. Examples of annuloplasty bands are shown in U.S. Pat. Nos. 5,824,066, and 6,786,924, and PCT International Patent Publication No. WO00/74603, the teachings of which are incorporated herein by reference.

Annuloplasty surgery associated with the tricuspid valve is generally intended to restore normal leaflet coaptation by reversing annulus dilation through plication. A way to restore leaflet coaptation is to restore the annulus to its normal or native shape during ventricular contraction or systole. However, the shape of the tricuspid annulus during portions of the cardiac cycle has not been well defined. Recent publications provide evidence that the tricuspid valve annulus has a non-planar or 3D structure, which is described as "saddle-shaped," and undergoes complex geometric changes during the cardiac cycle. (See, Fukuda et al. (2006), Three Dimensional Geometry of the Tricuspid Annulus in Healthy Subjects and in Patients with Functional Tricuspid Regurgitation: A Real-Time, 3-Dimensional Echocardiographic Study, *Circulation*, 114: 492-498; Ton-Nu et al. (2006), Geometric Determinants of Functional Tricuspid Regurgitation: Insights From 3-Dimensional Echocardiography, *Circulation*, 114:

143-149; Hiro et al. (2004), Sonometric Study of the Normal Tricuspid Valve Annulus in Sheep, *The Journal of Heart Valve Disease*, 13(1): 452-460).

In close proximity to the tricuspid valve is the atrioventricular (AV) node 28 (FIG. 1). The AV node is a section of nodal tissue that delays cardiac impulses from the sinoatrial node to allow the atria to contract and empty their contents and also relays cardiac impulses to the atrioventricular bundle. In order to maintain AV node function, during annuloplasty surgery, a surgeon generally attempts to avoid suturing in or near the AV node. Annuloplasty bands, or C-rings, are, therefore, good choices for use in repair of the tricuspid valve. The annuloplasty bands include a break or opening that may be generally positioned in the area including the AV node in order to avoid the need for suturing in that area. However, since the AV node is not visible to the surgeon, there is the possibility that while securing the endpoints of the annuloplasty band, sutures may be placed in tissue including the AV node.

The AV node is situated in the lower atrial septum at the apex of a triangle known as the Triangle of Koch (TOK), which is an area of heart tissue framed or bounded by certain anatomical landmarks in the heart. Two sides of the TOK are formed by the tendon of Todaro and the septal aspect of the tricuspid annulus. The base is marked at one end by the coronary sinus orifice and the other end by the septal annulus. The region known as the TOK has been the focus of research relating to the cure of supraventricular arrhythmias that arise near the AV node. Additionally, surgical and catheter ablation techniques have made use of the TOK as an anatomic landmark for ablation.

Despite multiple annuloplasty methods and devices currently on the market, there is a continued desire to improve such methods and devices. Particularly, there is a desire to have devices and methods that better accommodate the anatomy of the heart and the shape of the heart throughout the cardiac cycle, and thereby improve results associated with valve repair surgery.

SUMMARY OF THE INVENTION

Embodiments of the present invention offer numerous advantages. One advantage is that the healthy, native shape of the tricuspid valve may be mimicked by the annuloplasty device of the present invention, which thereby may improve function of the heart valve into which the annuloplasty device is implanted. This close match of normal anatomical shape could also increase durability of the repair by reducing stress on the leaflets. Another advantage is that the annuloplasty device can reduce stress on other parts of the heart, such as the aortic valve for example, and thereby may improve the function of the heart into which it is implanted. An additional advantage is that the annuloplasty device can allow for a greater degree of plication of certain regions of the annulus to improve the function of the tricuspid valve. In particular, the annuloplasty device may reduce the size of the posterior aspect of the annulus, which may thereby improve the function of the tricuspid valve. Yet another advantage of the present invention is that desired placement of the endpoints of the annuloplasty device can be determined in order to avoid the AV node, such that electrical conductivity through the heart is not affected by the device or sutures used to secure the device in place.

One aspect of the present invention is an annuloplasty device. One embodiment is an annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first and second ends; wherein the ring body is curvilinear, with substantially no flat portions, forming a shape, and the ends are configured such that when the device is implanted, the first end will be located near the junction of the septal and anterior aspects of the annulus and the second end will be located along the septal aspect of the annulus. The anterior portion may comprise a curve extending in a superior direction, the posterior portion may comprise a curve extending in the superior direction, the anterior portion curve may extend farther in the superior direction than the posterior portion curve. The shape of the ring body may mimic the shape of a native tricuspid valve annulus. The curvilinear shape may include varying slope between four slope minima. The ring body may follow a path from first end to second end that contains at least two maximum and two minimum positions along the path. The ring body may comprise a semi-rigid material. The ring body may further comprise: a sheath; and, a stiffening element disposed within the sheath. Upon implantation, the ends of the ring body may avoid the AV node of the heart. Upon implantation, the ends of the ring body may avoid the Triangle of Koch of the heart. Upon implantation, the device may reduce the posterior aspect of the annulus. Upon implantation, the device may reduce the septal-lateral, otherwise known as the septal-anterolateral, aspect of the annulus.

Further embodiments of the first aspect are an annuloplasty device for implantation adjacent an annulus of a tricuspid valve of a heart, the tricuspid valve having a flow orifice, and the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and an inward curve in the anterior portion such that when the device is implanted the curve will be located near an aortic valve of the heart and extends inward toward the flow orifice of the tricuspid valve.

Another aspect of the present invention includes related methods. One embodiment is a method of determining a shape of an annuloplasty device for tricuspid valve repair, the method comprising the steps of: determining specific anatomical features of a heart; determining the shape of the tricuspid valve annulus in the heart; and using the anatomical features of the heart and shape of the annulus to determine the shape of the annuloplasty device. At least one of the determining steps may be performed using at least one imaging technique on at least one heart. The at least one imaging technique may be selected from the group consisting of: radiographic means, echogenic means, computed tomography, and magnetic resonance imaging. The method may further comprise the steps of: using the anatomical features of the heart to determine the Triangle of Koch; and locating free ends of the device such that the free ends will not contact the Triangle of Koch when the device is implanted.

It is also contemplated by the present invention that the features of the embodiments described above or elsewhere herein may be combined.

BRIEF DESCRIPTION OF THE DRAWINGS

The present invention will be further explained with reference to the appended Figures, wherein like structure is referred to by like numerals throughout the several views, and wherein.

DETAILED DESCRIPTION OF PREFERRED EMBODIMENTS

An annuloplasty device in accordance with the present invention is a non-planar or 3D annuloplasty device. Studies have shown that a functioning tricuspid valve annulus is non-planar, and thus the present invention is particularly suited for repair of the tricuspid valve. Preferably, the annuloplasty device of the present invention mimics either one or both of the 2D and 3D shapes of a healthy, native tricuspid valve annulus, and preferably mimics the shape of a healthy, native valve annulus while in a portion of the cardiac cycle. Most preferably, the annuloplasty device mimics the shape of the healthy, native tricuspid valve annulus while the heart is in systole. The present invention also includes methods of determining the shape of such an annuloplasty device.

The annuloplasty device of the present invention preferably terminates in free ends that when implanted in a tricuspid valve annulus avoid conductive tissue, such as the AV node. An opening or gap in the annuloplasty device between free ends is preferably positioned adjacent the AV node to avoid the need for suturing in that area of the heart. Such an opening or gap may also facilitate appropriate surgical attachment of the device to the annulus when a catheter and/or pacing lead has been placed through the tricuspid valve prior to the surgical procedure. The present invention also includes methods of determining the preferred location of such free ends of the annuloplasty device.

The embodiments of the present invention as shown in the accompanying figures and described herein are particularly designed for or relate to the tricuspid valve. However, the present invention is not limited for application to the tricuspid valve, and it is contemplated that variations of the embodiments may apply to other valves.

Figure 1:
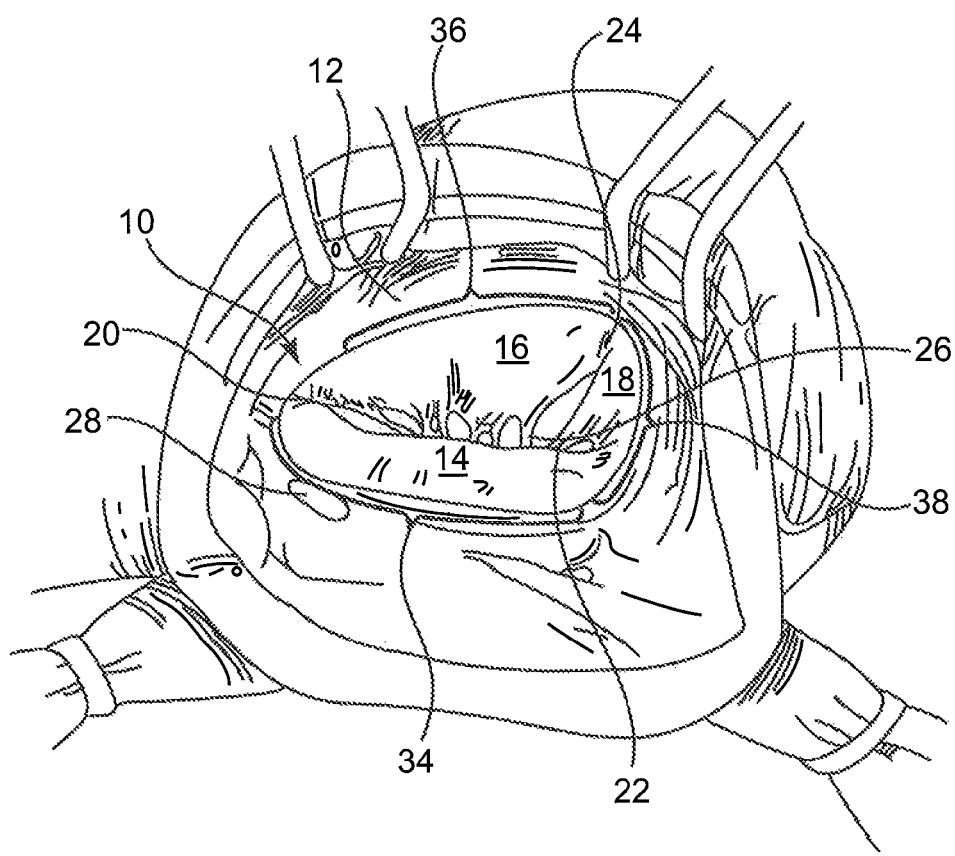
FIG. 1 is a plan view of a tricuspid valve and surrounding anatomy.
Figure 2:
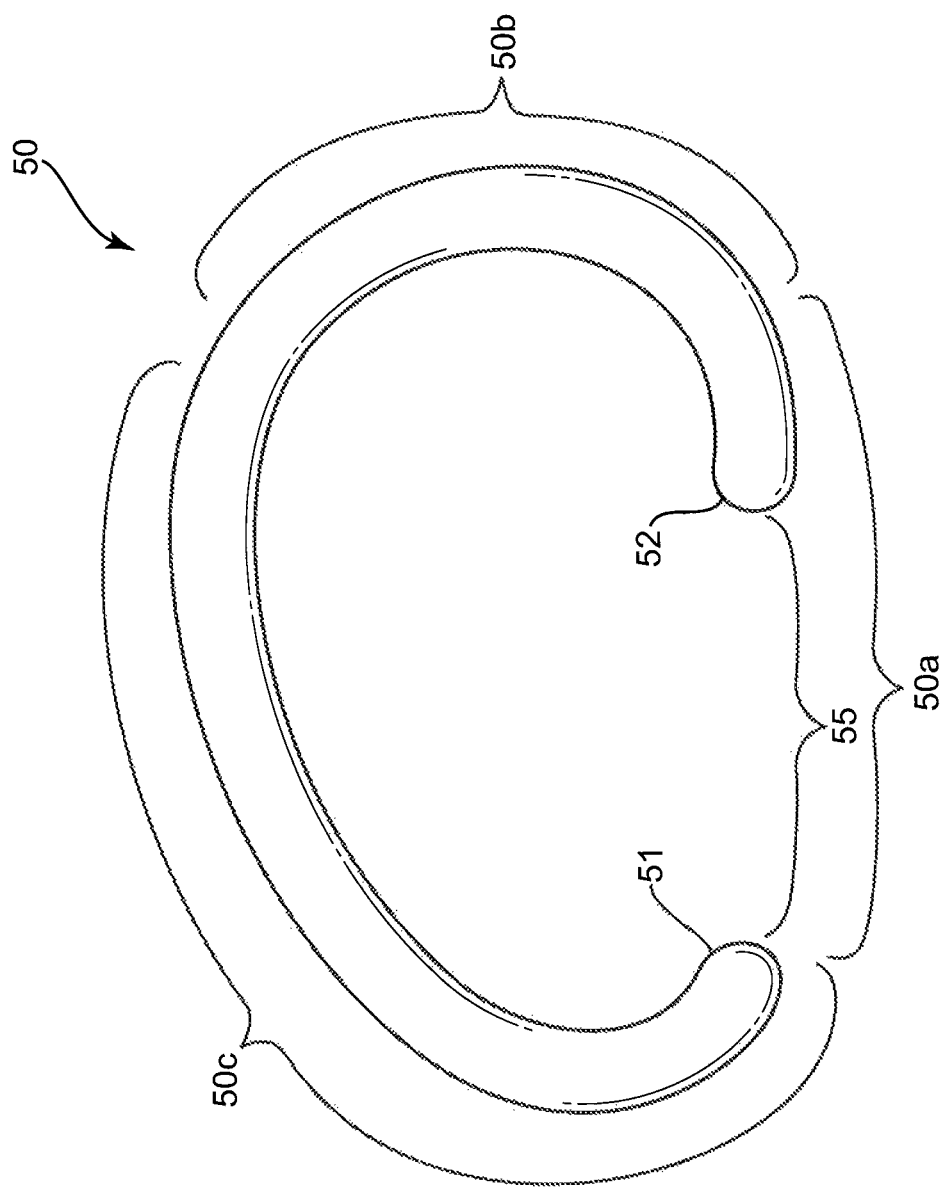
FIG. 2 is a top view of an exemplary annuloplasty band of the present invention.
Figure 3:
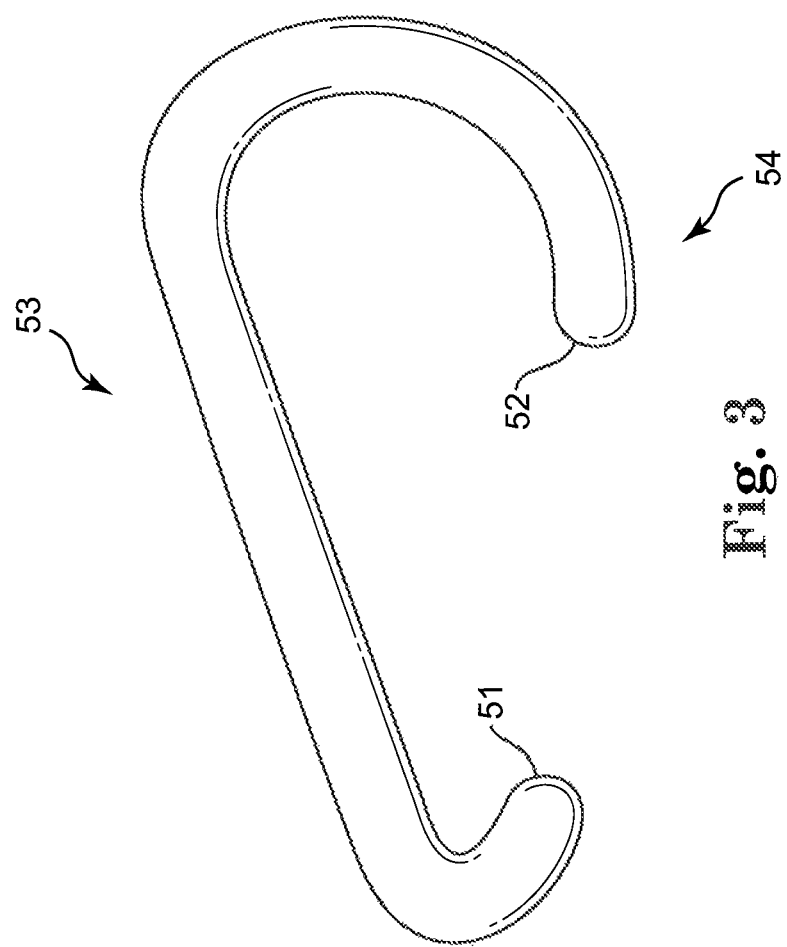
FIG. 3 is an isometric view of the exemplary annuloplasty band of FIG. 2.

With reference to the accompanying figures, wherein like components are labeled with like numerals throughout the several figures, and, initially, to FIGS. 2-6, one embodiment of the first aspect of the present invention is illustrated. FIG. 2 illustrates a top plan view of an annuloplasty band 50. Annuloplasty band 50 is generally arcuate (C-shaped), from a top view, as shown in FIG. 2. Annuloplasty band 50 includes a septal portion 50a adapted to generally be implanted on the septal aspect of a tricuspid valve, a posterior portion 50b adapted to generally be implanted on the posterior aspect of the tricuspid valve, and an anterior portion 50c adapted to generally be implanted on the anterior aspect of the tricuspid valve. The boundaries of the septal, posterior and anterior portions 50a, 50b, 50c of the band 50 are not definite, however, since the drawing may not be to scale and because the anatomy of individual patients may be different (e.g., the lengths of the aspects of different patients' valve annuli may be different).

As discussed earlier, the terms anterior and posterior, with regard to the leaflets of the valve, are also referred to as anterosuperior and inferior, respectively. Both terms may be used interchangeably. However, the present application will use the terms anterior and posterior.

When implanted, a first free end 51 and a second free end 52 of the annuloplasty band 50 may preferably be sutured to the septal aspect of the annulus. An opening or gap 55 is preferably present between the two free ends 51, 52. Such an opening or gap preferably may cooperate with the region of the annulus between the anteroseptal and posteroseptal commissures (i.e., the septal portion of the annulus). An opening or gap length can range between 0 mm (with the free ends touching) and the full distance between the anteroseptal and posteroseptal commissures.

FIGS. 3-6 illustrate an isometric view, a side view, a view from the anterior portion end and a view from the posterior portion end, respectively, of the annuloplasty band 50 of FIG. 2. FIGS. 3-6 show that the annuloplasty band 50 preferably has a 3D shape that has a sloped profile in the directions superior and inferior to the tricuspid valve annulus. The term "superior" as used herein refers to above the tricuspid valve annulus. The term "superior direction" as used herein refers to the direction extending above the tricuspid valve annulus, meaning generally towards the head while the tricuspid valve annulus is in place and oriented in the body. The term "inferior" as used herein refers to below the tricuspid valve annulus. The term "inferior direction" as used herein refers to the direction extending below the tricuspid valve annulus, meaning generally towards the feet while the tricuspid valve annulus is in place and oriented in the body. The 3D shape shown is one exemplary shape/configuration, however, other 3D shapes are also contemplated by the present invention, which may mimic the native, healthy shape of the tricuspid valve annulus and/or that may improve function of the tricuspid valve.

Figure 4:
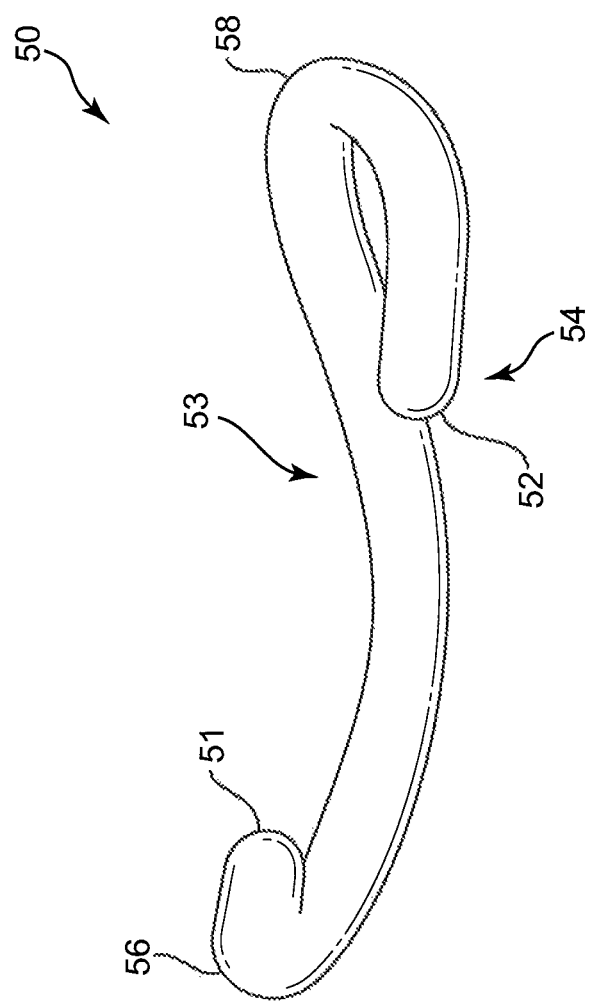
FIG. 4 is a side view of the exemplary annuloplasty band of FIG. 2.
Figure 5:
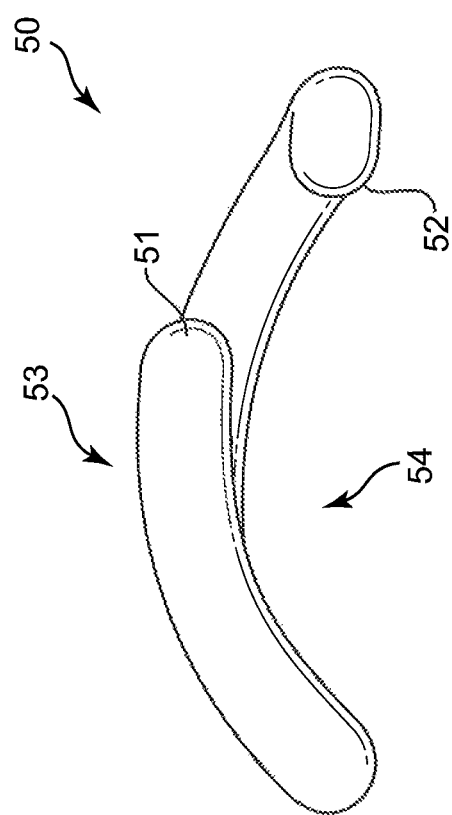
FIG. 5 is a view from anterior portion end of the exemplary annuloplasty band of FIG. 2.
Figure 6:
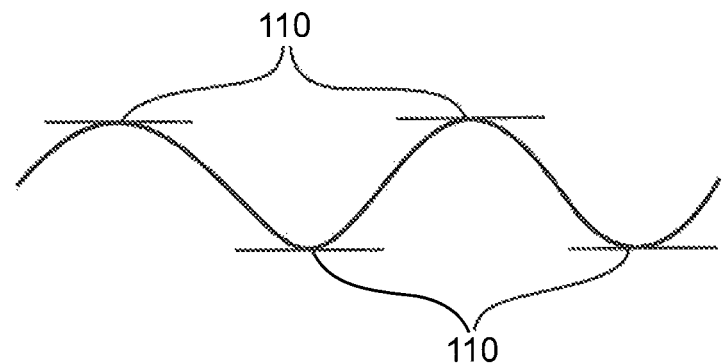
FIG. 6 is a schematic view of a stiffening element of the device of the present invention that has been opened and laid out providing a 2D view of the circumferential side view of the stiffening element, showing slope minima.

First 53 and second 54 sides of the annuloplasty band 50 are indicated in FIGS. 4-6. If the annuloplasty band 50 was implanted in a valve annulus, blood flow would generally flow through from first side 53 to second side 54. In other words, if implanted, the first side 53 of the annuloplasty band 50 is preferably adjacent the atrial side of the valve and the second side 54 is preferably adjacent the ventricular side of the valve. Blood flow should be from superior to inferior or in the inferior direction as defined above.

The embodiment shown in FIGS. 2-6 includes an opening or gap 55 of a certain size. Different embodiments of the annuloplasty device of the present invention may have different sized openings or gaps between two free ends of the annuloplasty device. The purpose of a smaller opening may be to provide additional support for anchoring the device to the valve annulus. The benefit of having a larger opening, however, may be that fewer sutures are necessary in the septal portion of annulus to attach the device, which reduces possible effects caused by suture placement in and around the AV node.

The preferred shape of the annuloplasty device of the present invention is substantially similar to the shape of a healthy, native tricuspid valve annulus. In general, the preferred shape is curvilinear and continuously varying or curving, and includes substantially no flat portions, from first free end to second free end. "Flat" means non-curved in any of three dimensions. The anterior, posterior and septal portions of the device together form the shape of the ring body. The anterior and posterior portions preferably comprise curves or bowing extending in a superior direction. The anterior portion curve or bow extends farther in the superior direction than does the posterior portion curve. The shape of the ring body preferably emulates or mimics the shape of a healthy, native tricuspid valve annulus. Most preferably, the shape is determined in systole. The band is preferably configured such that the first and second free ends 51, 52, when sutured to the annulus, are located at or near the anteroseptal commissure and along the septal aspect of the annulus, respectively.

With reference to FIGS. 2-6, one example of the preferred curvilinear and continuously varying or curving shape of the device as described above is shown. The band 50 comprises a curvilinear shape with a curve 56 (FIG. 4) in the anterior portion extending in the superior direction and a curve 58 (FIG. 4) in the posterior portion also extending in the superior direction. The anterior portion curve 56 extends farther in the superior direction than does the posterior portion curve 58. Preferably, the curve 56 in the anterior portion may be sutured at or near the aortic valve when the device is implanted in an annulus. The shape in FIGS. 2-6 is believed to emulate the shape of a healthy, native tricuspid valve annulus. However, other possible shapes are also contemplated.

In the case of an annuloplasty device of the present invention that includes two free ends, their preferred location is as follows: the first free end being configured and sized for a select tricuspid valve size to be located near the junction of the anterior and septal portions; and, the second free end being located along the septal portion. The first and second free ends, when the device is implanted in an annulus, will preferably correspond to the anteroseptal commissure (junction of anterior and septal aspects) and the septal portion, respectively. Another preferred location for the two free ends is that both free ends will be located in the septal portion of the device and, when implanted, correspond to the septal aspect of the annulus. Preferably the two free ends are to be located to avoid suturing of the ends near the area of the heart that includes the AV node, which could negatively affect conductivity relating to the AV node.

With reference to FIG. 2, the first free end 51 is generally shown at or near the junction of the anterior portion 50c and the septal portion 50a or near the anteroseptal commissure when implanted. The second free end 52 is generally shown in the septal portion 50a. The figure is not, however, to scale, and represents one location for the two free ends 51, 52. Other locations for the free ends of an annuloplasty band in accordance with the present invention are, however, also contemplated by the present invention.

The annuloplasty device of the present invention may include various 3D shapes. As described above, a preferred 3D shape is curvilinear and continuously curving around its perimeter with substantially no flat portions. The preferred shape includes a curve in the anterior portion that extends in the superior direction and a curve in the posterior portion that extends in the superior direction, with the anterior portion curve extending farther in the superior direction than the posterior portion curve. The curve in the anterior portion is preferably configured to be located near the aortic valve when the device is implanted around a tricuspid valve annulus.

In another embodiment, however, the 3D shape of a device, for example, may be described as a curvilinear shape with a generally varying slope between four minima (e.g., slope minima). The 3D, curvilinear slope is defined in the directions superior and inferior with respect to the tricuspid annulus. FIG. 6 schematically and generally illustrates this concept by showing a stiffening element of the present inventive device that has been opened and laid out, providing a 2D view of the circumferential (or perimeter) side view. The "slope minima" and "minima" and "minimum slopes" referred to with regard to FIG. 6 are indicated by 110. The location of the minimum slopes 110 can be varied around the perimeter of the ring corresponding to specific anatomical locations in order to preferably mimic a natural anatomic shape, which may provide improved valve function and reduce leaflet stress. A period in the curvilinear shape between the slope minima 110 can also be adjusted by increasing or decreasing the rate of slope change between the four slope minima 110, which may allow for both variable amplitude and spacing between slope minima 110. The spacing between neighboring slope minima 110 preferably is at least one eighth of the perimeter of the device and is preferably no greater than half the perimeter of the device, which may control the amplitude and slope between neighboring slope minima 110.

Figure 7:
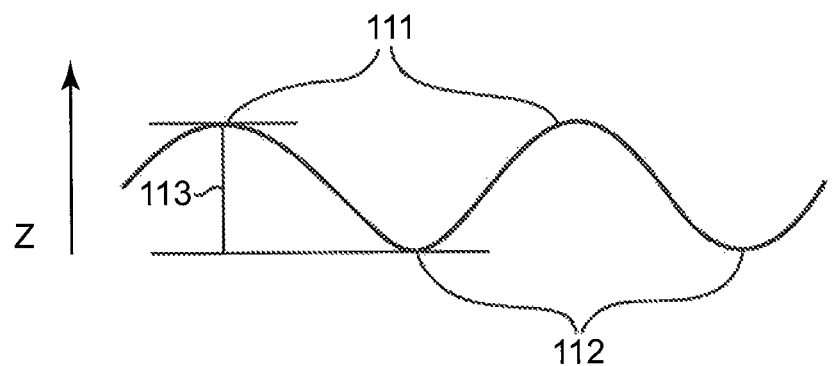
FIG. 7 is a schematic view of a stiffening element of the device of the present invention that has been opened and laid out providing a 2D view of the circumferential side view of the stiffening element, showing maximum and minimum positions and range between them.

In another embodiment, the 3D shape of the device may be described as a curvilinear shape that follows a path around the perimeter of the ring that contains at least two maximum and two minimum positions along the path. FIG. 7 schematically illustrates this embodiment by showing a side view of a stiffening element of the present inventive device that has been opened and laid out providing a 2D view of the circumferential side view of the stiffening element. The maximum positions 111 and minimum positions 112 can occur at desired positions along the perimeter of the device and correspond to desired positions along the annulus in order to preferably mimic the natural anatomical shape of the annulus, which may provide improved valve function and reduce leaflet stress. A preferred range 113 between any maximum 111 and minimum 112, as shown in FIG. 7, may be no less than 10% of the linear distance 114 between the anteroseptal 115 and posteroseptal 116 commissures, as shown with regard to an annulus 119 in FIG. 8.

Figure 8:
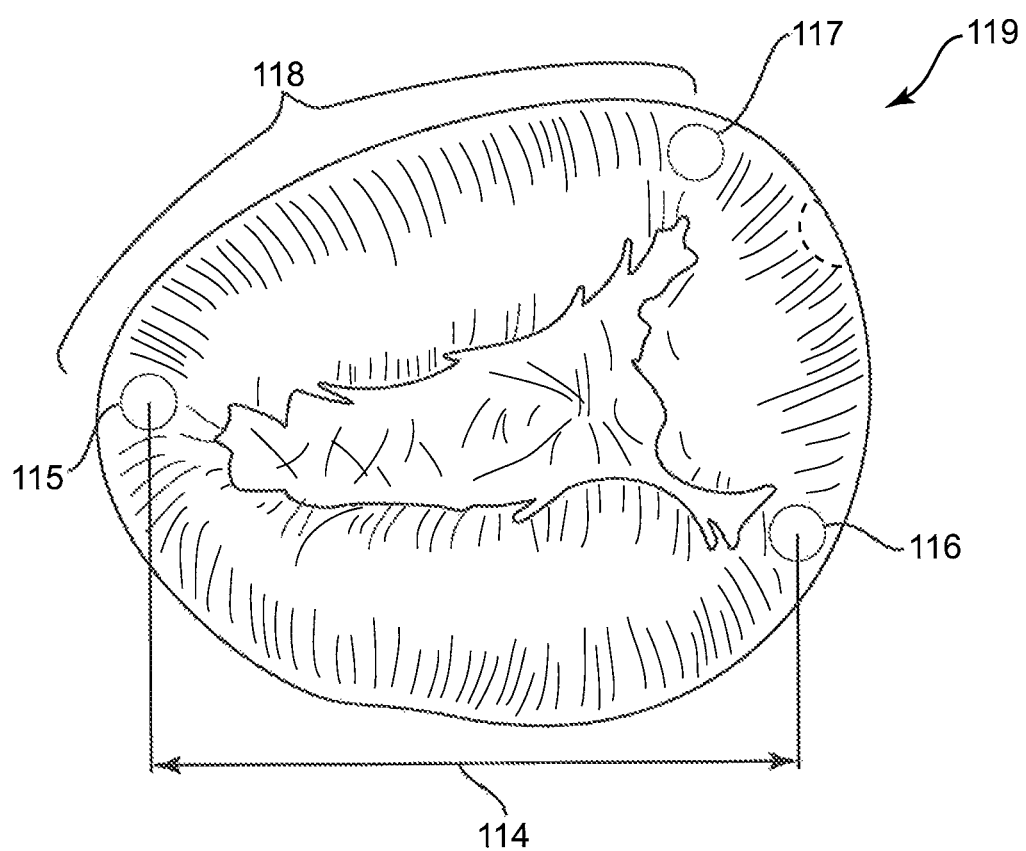
FIG. 8 is a top view of a tricuspid valve annulus, indicating positions of the commissures.

In yet another embodiment, the 3D shape of the device may be described as a curvilinear, and 3D or non-planar ("non-planar" defined in the directions superior or inferior with respect to the tricuspid annulus) shape along a span of the device that mates with an annular region 118 of an annulus 119, as that shown in FIG. 8 with the annular region 118 extending between the anteroseptal 115 and anteroposterior commissures 117. The non-planar shape may preferably span at least 30% of the arc length (i.e., length of the annulus along the perimeter of the annulus) between the anteroseptal 115 and anteroposterior 117 commissures, with a minimum height (extending in the directions superior or inferior with respect to the tricuspid annulus) above or below the annulus 119 of at least 5% of the linear distance 114 between the anteroseptal 115 and posteroseptal 116 commissures.

The annuloplasty device of the present invention comprises a ring body that comprises a sheath or covering and a stiffening element within the sheath or covering. The annuloplasty device body preferably further comprise an opening or gap between two free ends of the covered stiffening element. Details of the components are provided below.

The stiffening element portion of the annuloplasty device of the present invention is preferably designed to be covered and implanted in a tricuspid valve annulus. In general, the stiffening element imparts a shape to the annuloplasty device, and is adapted to remodel, preferably, the tricuspid valve annulus. The stiffening element may comprise a metal, ceramic, polymer or a composite, for examples. Some desirable properties of suitable materials for use in the stiffening element include, but are not limited to, biocompatibility, biostability, and corrosion- and fatigue-resistance. In some embodiments, the stiffening element is made of a material that imparts rigidity to the stiffening element, which in turn imparts rigidity to the annuloplasty band. If the stiffening element comprises a metal wire, the wire can be formed of any medically-acceptable, implantable, biocompatible metal, such as cobalt-nickel alloy (MP35N™), cobalt-chromium alloy (Elgiloy™, Haynes 25™), titanium, stainless steel, shape memory materials such as nickel-titanium alloy (Nitinol™), or other similar inert biocompatible metal.

The stiffening element may generally have a circular cross-section. However, cross-sections of other shapes are also contemplated by the present invention (e.g., square, rectangular, elliptical, triangular, or the like). Different cross-sectional shapes can be used to impart varying degrees of bending or torsional stiffness depending on the bending/twisting plane with respect to the section modulus. Also, the cross-sectional shape may be varied around the perimeter of the stiffening element, which may vary the stiffness around the perimeter.

Preferably, the stiffening element may be covered or over-molded with a biocompatible, biostable, implantable medical grade elastomeric protective coating, such as an elastomeric thermoplastic polymer (e.g., polyurethane) or a silicone (e.g., liquid silicone rubber) to provide a consistent profile and to create desirable needle penetration properties for the surgeon. Also, coating can impart radiopaque and echogenic in vivo visualization, for example. Alternatively, the protective coating may be tubing within which the stiffening element is disposed, the tubing consisting of biocompatible, biostable, implantable medical grade elastomeric material, such as elastomeric thermoplastic polymer (e.g., polyurethane) or silicone. In yet other embodiments, the protective coating may be eliminated.

The stiffening element, with or without the protective coating, is preferably covered with a sheath or covering. The covering or sheath may comprise a knitted polymeric fabric (e.g., polyethylene terephthalate or Dacron™), although woven, non-woven materials (e.g., spun-bond, melt-blown, staple fiber matrix, etc.), braided fabrics, or metallic braids (e.g. titanium, Nitinol, and stainless steel wires) are also contemplated, as well as sheaths formed of harvested biological tissue (e.g., pericardial tissue). The covering or sheath may optionally be provided with any of various biocompatible coatings. The preferred purpose of the covering or sheath is to provide a site for attachment of the device to the annulus using invasive or minimally invasive surgical techniques as well as to allow for in-growth of the device with the native valve tissue. A plurality of knotted sutures is typically used to secure the annuloplasty device to the tricuspid annulus, although other fasteners such as staples, fibrin glue, or the like may be used.

The stiffening element may also be radiopaque, echogenic, MRI-compatible and/or otherwise imaging enhanced so that it may readily be visualized after implantation using various existing techniques or any future developed techniques, including x-ray, MRI, echogram, etc. By "radiopaque," it is meant that the material or element prevents the passage of radiation. "Radiation" is meant to include electromagnetic energy, light, etc. By "echogenic," it is meant that it reflects sound waves. By "MRI-compatible" it is meant that the material or element is both MRI safe and capable of being excited by MRI.

The annuloplasty device of the present invention may have any amount of flexibility. Preferably, the device has a sufficient elasticity that allows the band to return to an original shape after physiologic forces are applied and removed to the device and the device is in a free state. For example, the device may be rigid or semi-rigid. The rigidity of the device may be varied depending upon the material comprising the device and/or the construction of the device. For example, the rigidity of the device can also be controlled by controlling the material and shape/size of the cross section of the stiffening element.

In some embodiments of the present invention, in particular any embodiments having a stiffening element comprising a semi-rigid material and two free ends, the stiffening element may have eyelets (not shown) at one or both of its two free ends, which may be used to suture the ends and anchor them to fibrous tissue of the annulus (e.g., the septum). The eyelets may be formed by the stiffening element being bent back onto itself at one or both of the first and second free ends. Alternatively, the eyelets may be integrally molded with the rest of the stiffening element, or can be subsequently assembled to the stiffening element. As used herein, "eyelet" means an opening with a substantially closed perimeter, but does not require a specific shape (e.g., an eyelet can be round, square, rectangular, trapezoidal, hexagonal, tear-drop, oval, elliptical, or any other suitable shape), although shapes with lower stress concentrations are preferred. The eyelets are preferably adapted to receive at least one suture to secure the annuloplasty device to a valve annulus or a heart valve, such as the tricuspid valve.

In some embodiments, construction of the annuloplasty device preferably provides a low profile attribute. More particularly, the cross-sectional diameter or width would preferably range from about 0.03 to about 0.20 inches, with the stiffening element portion having a cross-sectional diameter or width ranging from about 0.005 to about 0.150 inches. However, other ranges of diameters and widths are also contemplated by the present invention. A purpose of the low profile is to minimize disturbance to blood flow and potential thrombus formation.

Figure 9:
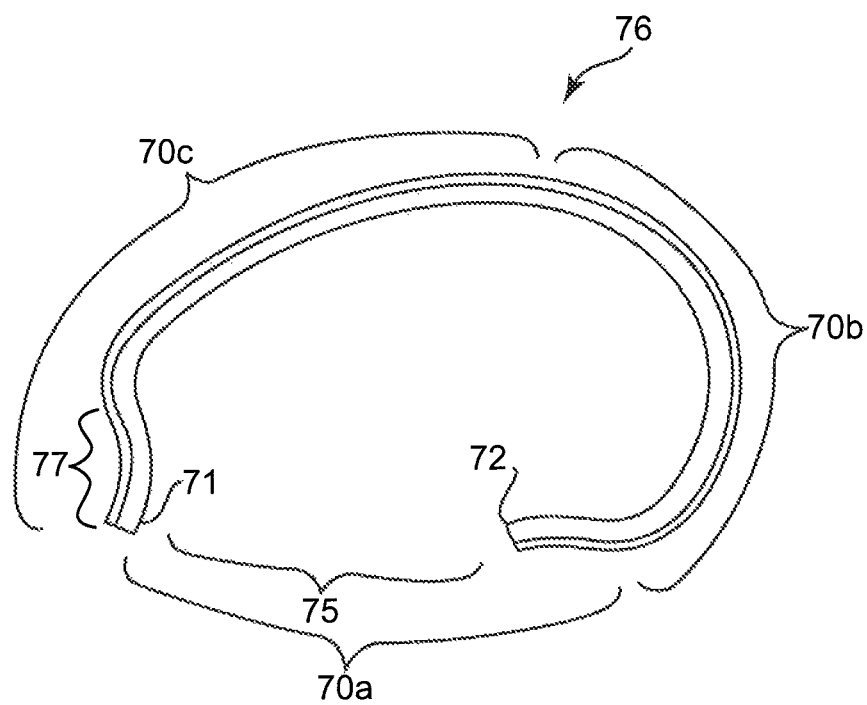
FIG. 9 is a top plan view of an exemplary stiffening element forming one structural component of an exemplary annuloplasty band of the present invention.

A stiffening element portion of another embodiment of the annuloplasty device of the present invention is shown in FIG. 9. The stiffening element 76, seen in a top plan view, has an opening or gap 75 between two free ends 71, 72 of the stiffening element, and an inward curvature 77 in the anterior portion 70c, which corresponds to an anterior aspect of an annulus, and near the first free end 71. The inward curvature 77 curves inward toward the flow or valve orifice in the region that may interface with an anterior aspect of an annulus and that may be located near an aortic valve when a device including the stiffening element 76 is implanted adjacent a tricuspid valve annulus. The inward curvature 77 can allow the aortic valve to open more fully because the stiffening element 76 of the device does not enter or protrude into the area of the aortic valve and avoids the aortic valve. As a result of avoiding the aortic valve, the curvature 77 can minimize distortion of the aorta during a cardiac cycle. This embodiment may be combined with the 3D shapes of the device that are described above.

Figure 10:
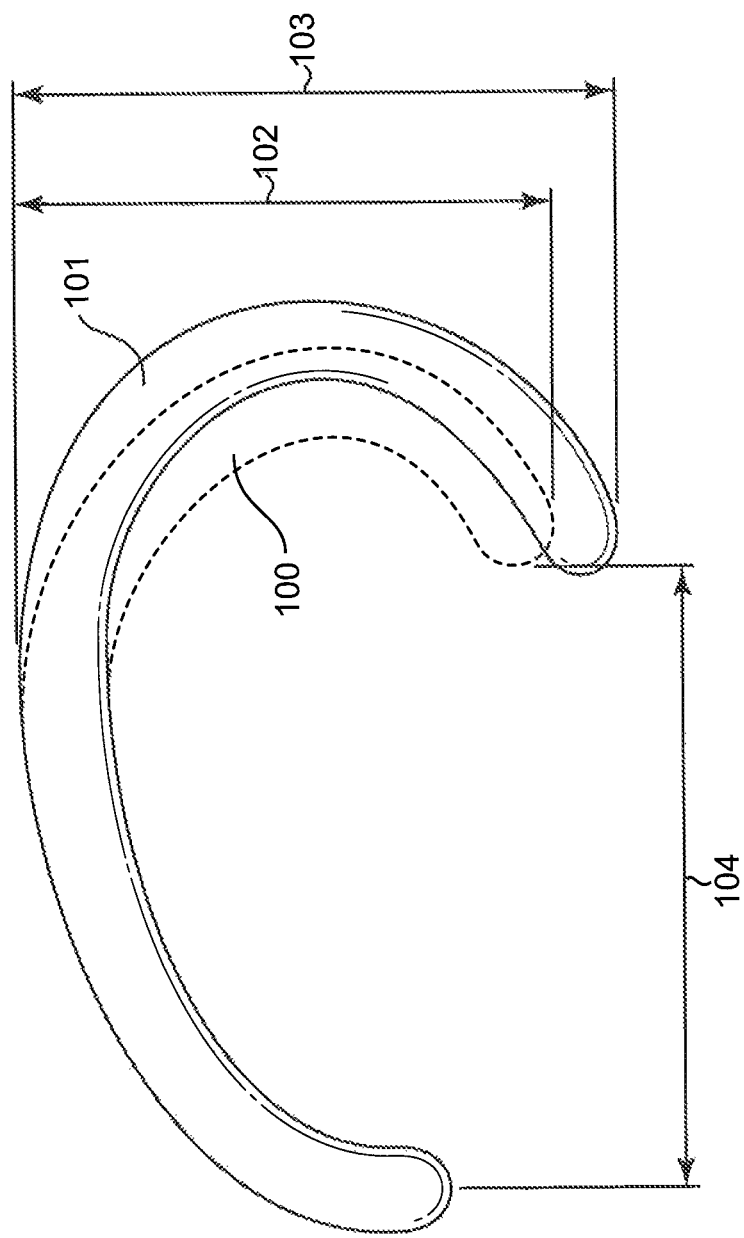
FIG. 10 is a top plan view of an exemplary annuloplasty band of the present invention shown overlapping an annuloplasty band of the same size but that includes a reduced posterior and anterior portion.

Another optional feature of the present invention allows for overcorrection of valve dilation along the posterior aspect of the tricuspid annulus by reducing the length of the posterior portion of a ring relative to a measured valve size. FIG. 10 illustrates how the length of the posterior annulus portion may be reduced to correct valve dilation. In FIG. 10, two annuloplasty bands 100 (demonstrating this embodiment of the present invention) and 101 (an exemplary prior art band) are laid one on top of the other so that the anterior portions and the free ends near the anterior portions are aligned. The septal-lateral, otherwise known as the septal-anterolateral, distance 102 of the portion of the stiffening element 100 corresponding to the posterior aspect of an annulus is shorter than the length 103 of the portion of stiffening element 101 corresponding to the posterior aspect. The distance 104 between the free ends in both stiffening elements 100, 101, however, for both bands is shown as substantially the same. As can be seen in FIG. 10, the reduction in the length of the posterior portion 102 from posterior length 103, while maintaining the distance between the free ends 104, results in a reduced curvature along the posterior region of the stiffening element 100 from stiffening element 101. Since the size of an annuloplasty device may be dependent upon the distance between the free ends, the result is a stiffening element 100 of generally the same size as stiffening element 101, but with a reduced curvature along the posterior portion. The purpose of this embodiment of the present invention is to ensure sufficient leaflet coaptation without global downsizing of the valve annulus. This embodiment may be combined with the 3D shapes of the device that are described above.

The present invention also contemplates a system that includes holders and sizers correlating in shape and size to the annuloplasty device of the present invention, which may differ in size and shape. Such holders assist in implantation of a ring or band in a patient, and such sizers assist in choosing the correct size of device for a given valve or valve annulus of a patient.

A second aspect of the present invention relates to methods of determining the shape and configuration of an annuloplasty device used to repair a tricuspid valve. One embodiment of the second aspect is a method of determining a shape of an annuloplasty device for tricuspid valve repair, the method comprising the steps of: determining specific anatomical features of a heart; determining the shape of the tricuspid valve annulus in the heart; and using the anatomical features of the heart and shape of the annulus to determine the shape of the annuloplasty device. At least one of the determining steps may be performed using at least one imaging technique on at least one heart. The at least one imaging technique may be selected from the group consisting of: radiographic means, echogenic means, computed tomography, magnetic resonance imaging, other currently existing imaging processes, or any future developed imaging techniques. The method may further comprise the steps of: using the anatomical features of the heart to determine the Triangle of Koch; and locating free ends of the device such that the free ends will not contact the Triangle of Koch when the device is implanted.

The Example below describes how the shape and configuration (including location of the ends) of the device may be determined. Other methods are contemplated by the present invention, however.

EXAMPLE

Six sets of human heart data were analyzed in order to assess the shape of the tricuspid valve annulus. Datasets included one MRI dataset (MRI1) collected during systole and five CT datasets (CT1-CT5) collected during an arbitrary portion of the cardiac cycle. The data collected were composed into Digital Imaging and Communication in Medicine (DICOM) (available from Laurel Bridge Software, Inc., located in Newark, Del., U.S.A.) image files, which were then imported into Mimics® software (available from Materialise, located in Belgium). Utilizing the Mimics® software, left and right sides of the heart, in the images, were segmented by differentiating image contrast between the blood volume within the heart chambers and the heart tissue. The image pixels from the image were grouped (i.e., color coded) based on defining levels of image contrast below which all pixels with contrast less than the defined level were grouped (i.e., thresholding), with remaining pixels above the contrast level grouped separately. After thresholding, the tricuspid valve annulus was identified and the shape reconstructed, and other anatomical landmarks or features in the heart were identified.

Figure 11:
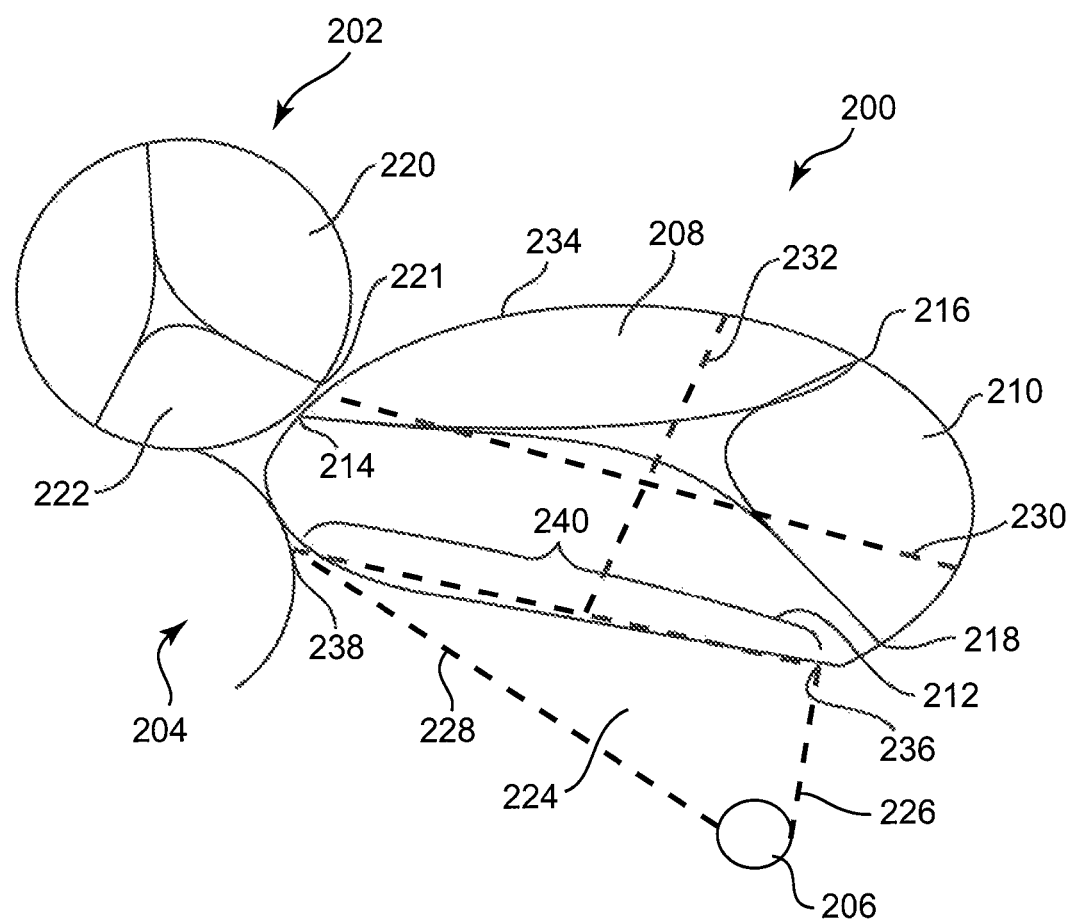
FIG. 11 is a schematic representation of the area of the heart near and including the tricuspid valve.

FIG. 11 is a schematic representation of the area of the heart near and including the tricuspid valve 200 from a superior perspective with respect to the annulus. The aortic valve 202 is schematically represented, as well as the membranous septum 204 of the heart, and the coronary sinus 206. The anterior 208, posterior 210 and septal 212 leaflets, and the anteroseptal 214, anteroposterior 216 and posteroseptal 218 commissures of the tricuspid valve 200 are also illustrated. Also, the right coronary cusp 220 and the non-coronary cusp 222 of the aortic valve 202 are shown. Between the two cusps is the right coronary/non-coronary commissure 221.

Figure 12:
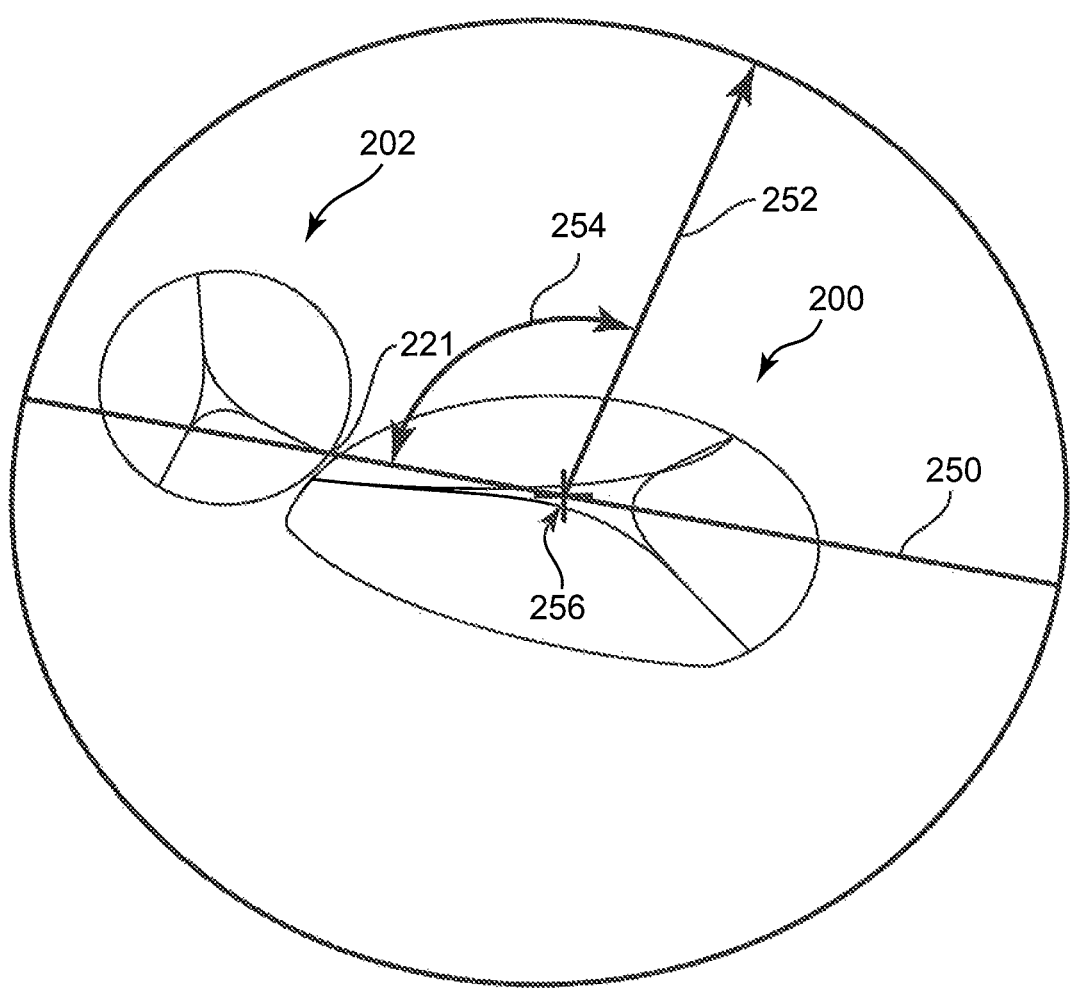
FIG. 12 is the schematic representation of FIG. 11 with lines demonstrating how the cylindrical coordinate system was established with regard to the tricuspid annulus.

Axes and other boundaries were constructed, as shown on FIG. 12, from anatomical landmarks in the heart, which were used in the analysis of the six datasets. A major axis 230 and a minor axis 232 of the tricuspid valve 200 were determined. Also, the Triangle of Koch (TOK) 224 was determined. The TOK height 226 (or base of triangle) extends between the coronary sinus orifice 206 and a point 236 normal to the coronary sinus orifice 102 along the septal aspect of the tricuspid annulus 234. The TOK length 228 (one side of triangle) extends between the coronary sinus orifice 206 and the location 238 where the septum 204 and the tricuspid valve 200 come together, and extends along the Tendon of Todaro of the heart. The second side of the triangle extends along the septal aspect of the annulus generally.

In the analysis, the tricuspid valve annulus 234 was identified by selecting two points on the annulus 234 in each image slice for image planes passing obliquely through the annulus, allowing for generation of an interpolated curve through the data points. Additionally, curves were generated for the aortic valve commissures, the coronary sinus orifice 206, and the TOK 224, which provided anatomic references or landmarks with respect to the tricuspid valve annulus.

From the reconstructed anatomic references or landmarks, measurements were made using the Mimics® software for each dataset, in order to categorize the annulus shape. The measurements included the major axis 230 and minor axis 232 dimensions of the valve annulus, the full annular perimeter, the partial annular perimeter 240 (clockwise perimeter with respect to the annulus region bounded by the TOK 224), TOK height 226, and TOK length 228. In addition to the measured values, ratios were computed for the minor-to-major axis diameters and the partial-to-full perimeters to assess the degree of annular circularity and the percentage of the annular perimeter adjacent to the conductive tissue along the septal aspect of the annulus. Tables 1 and 2 below provide measurements and averages, standard deviations, maxima and minima for the 5 CT datasets (CT1-CT5) and the 1 MRI dataset (MRI1).

TABLE 1

Measurements made in Mimics ® software for each of the six datasets.

| Case | Full Perimeter (mm) | Partial Perimeter (mm) | Major (mm) | Minor (mm) | TOK H (mm) | TOK L (mm) |
|---|---|---|---|---|---|---|
| CT1 | 102.48 | 75.79 | 35.89 | 23.79 | 6.86 | 26.69 |
| CT2 | 104.77 | 85.52 | 32.68 | 31.57 | 6.06 | 19.25 |
| CT3 | 120.54 | 103.01 | 42.60 | 35.23 | 6.19 | 17.53 |
| CT4 | 127.96 | 110.89 | 41.80 | 39.33 | 12.90 | 17.07 |
| CT5 | 135.97 | 111.45 | 43.32 | 37.22 | 12.87 | 24.52 |
| MRI1 | 147.26 | 126.02 | 49.19 | 42.99 | 14.29 | 21.24 |
| Average | 123.16 | 102.11 | 40.91 | 35.02 | 9.86 | 21.05 |
| STD | 17.55 | 18.47 | 5.85 | 6.71 | 3.87 | 3.88 |
| Max | 147.26 | 126.02 | 49.19 | 42.99 | 14.29 | 26.69 |
| Min | 102.48 | 75.79 | 32.68 | 23.79 | 6.06 | 17.07 |

TABLE 2

Ratios computed from minor/major axis dimensions and partial/full perimeters.

| Case | Minor:Major Axis Ratio | Partial:Full Perimeter Ratio |
|---|---|---|
| CT1 | 0.66 | 0.74 |
| CT2 | 0.97 | 0.82 |
| CT3 | 0.83 | 0.85 |
| CT4 | 0.94 | 0.87 |
| CT5 | 0.86 | 0.82 |
| MRI1 | 0.87 | 0.86 |
| Average | 0.85 | 0.83 |
| STD | 0.12 | 0.05 |
| Max | 0.97 | 0.87 |
| Min | 0.66 | 0.74 |

The curves generated for the tricuspid annulus, the aortic commissures, and coronary sinus orifice were outputted from the Mimics® software as 3D points in Cartesian coordinate format, with the coordinate system referenced to MRI and CT scanners that were used. Using DPlot software (available from HydeSoft Computing, LLC, located in Vicksburg, Miss., U.S.A.), a plane was computed for the tricuspid annulus points in 3D space using a least squares based algorithm. From the DPlot computed plane, residual offset (vertical offset) of each point from the plane was computed to assess the non-planarity of the annulus, with the maximum residual offset (positive direction), minimum residual offset (negative direction), and residual offset range computed for each dataset. Table 3 provides the residual offset maxima, minima and ranges for each dataset, and also provides the averages, standard deviations, maxima and minima.

TABLE 3

Residual offsets of tricuspid annulus data points from DPlot computed plane for each dataset.

| Case | Residual Offset Max (mm) | Residual Offset Min (mm) | Reisudal Offset Range (mm) |
|---|---|---|---|
| CT1 | 2.79 | −4.00 | 6.78 |
| CT2 | 6.79 | −6.19 | 12.98 |
| CT3 | 4.90 | −4.77 | 9.67 |
| CT4 | 12.70 | −9.95 | 22.65 |
| CT5 | 4.27 | −5.40 | 9.67 |
| MRI1 | 4.58 | −4.82 | 9.40 |
| Average | 6.00 | −5.85 | 11.86 |
| STD | 3.52 | 2.14 | 5.64 |
| Max | 12.70 | −4.00 | 22.65 |
| Min | 2.79 | −9.95 | 6.78 |

To assess the normal distance of each tricuspid annulus point from a computed plane, the annulus curves for each dataset were loaded into Pro/ENGINEER (available from Parametric Technology Corporation, located in Needham, Mass., U.S.A.). The computed plane from D-Plot was duplicated in Pro/ENGINEER using the coefficients of the plane equation computed from D-Plot. A Cartesian coordinate system was then defined in Pro/ENGINEER, with the z-axis normal to the computed plane, and the x and y axes contained within the plane. The coordinate data of annulus points with respect to the newly defined coordinate system were outputted to Excel (available from Microsoft Corporation, located in Redmond, Wash., U.S.A.) to determine the normal distance (z-coordinate) of the points with respect to the Pro/ENGINEER computed plane, with maximum, minimum, and range reported.

Finally, to locate maximum and minimum z-coordinate points in 3D space, a local cylindrical coordinate system $(r,\theta,z)$ was defined for each dataset separately. FIG. 12 is a schematic representation showing how the cylindrical coordinate system was defined with regard to the schematic representation of FIG. 11, in order to locate maximum and minimum z-coordinates along the tricuspid annulus. Center point 256 is the centroid of the annulus coordinates in x and y. The line 250 though the center point 256 (diameter of the circle) is an axis through the center point 256 and the peak 221 of the right coronary/non-coronary aortic valve commissure. The line 252 is showing a radius (r) and the line 254 is showing the positive angular direction ($\theta$) (clockwise) from the line 250 to the line 252. The plane of the drawing in FIG. 12 is the $\theta$ plane, with the z-axis extending normal to the drawing. The curves for the aortic valve and tricuspid annulus were loaded into Pro/ENGINEER for the analysis. The center point 256 for the coordinate system was defined by centering the x-y Cartesian coordinates of the annulus points such that the average of difference of individual x and y coordinates from the average x and y coordinates equals zero. Using the computed plane originally defined for the tricuspid annulus, axes were defined normal to the plane vertically through the center point of the annulus, and through the center point and the peak point of the aortic valve commissure between the right coronary non-coronary cusps. First, the magnitude and angular position of the maximum and minimum z-coordinates within each dataset were located (Max 1 and Min 1, in Table 4). Second, the datasets were truncated or excluded from the center point of the tricuspid valve annulus toward the aortic valve side of the annulus, and the magnitude and angular position of the second maximum and minimum z-coordinates were located (Max 2 and Min 2, in Table 4).

TABLE 4

1st and 2nd maximum and minimum z-coordinates for each dataset along with angular position in cylindrical coordinate system.

|  | Max1 | | Max 2 | | Min1 | | Min2 | |
| --- | --- | --- | --- | --- | --- | --- | --- | --- |
| Case | z (mm) | θ Position (deg) | z (mm) | θ Position (deg) | z (mm) | θ Position (deg) | z (mm) | θ Position (deg) |
| CT1 | 1.4 | −109.5 | 1.2 | 112.8 | −2.0 | 182.9 | −0.9 | 329.9 |
| CT2 | 1.9 | 7.2 | 0.9 | 124.5 | −1.8 | 56.6 | −1.6 | 254.7 |
| CT3 | 2.1 | −78.1 | 1.4 | 213.0 | −2.1 | 21.8 | −1.4 | 86.8 |
| CT4 | 2.6 | 10.2 | 1.0 | 158.6 | −2.0 | 247.0 | −1.0 | 55.2 |
| CT5 | 1.6 | −26.7 | 1.8 | 185.4 | −2.2 | 267.2 | −1.6 | 110.0 |
| MRI1 | 3.9 | −82.7 | 1.6 | 129.9 | −3.7 | 255.1 | −3.0 | 57.1 |
| Average | 2.3 | −46.6 | 1.3 | 154.0 | −2.3 | 171.8 | −1.6 | 149.0 |
| STD | 0.9 | 50.5 | 0.3 | 39.1 | 0.7 | 107.3 | 0.8 | 115.3 |
| Max | 3.9 | 10.2 | 1.8 | 213.0 | −1.8 | 267.2 | −0.9 | 329.9 |
| Min | 1.4 | −109.5 | 0.9 | 112.8 | −3.7 | 21.8 | −3.0 | 55.2 |
| Range | 2.5 | 119.7 | 0.8 | 100.2 | 1.9 | 245.4 | 2.1 | 274.6 |

From analysis of the data, general trends were observed. The ratio of the minor-to-major axis diameters showed that the annuli were non-circular for the cases analyzed, with a maximum ratio of 0.97, a minimum of 0.66, and an average value of 0.85. The partial:full perimeter ratios showed a maximum of 0.87, and minimum of 0.74, and an average of 0.83, indicating that the conductive tissue region makes up approximately 17% of the annular perimeter. The residual offset data indicated clearly that the annulus is non-planar, with the average maximum and minimum approximately 6 mm and the range approximately 12 mm. The maximum and minimum z-coordinate data indicated average normal offsets of Max 1 and Min 1 data points from the computed plane of approximately 2.3 mm, with Max 2 and Min 2 offset by 1.3 and 1.6 mm, respectively. By locating the positions of the maximum and minimum z-coordinates, the results showed the largest positive z-coordinate along the annulus was generally located near the aortic valve, counterclockwise from the right coronary/non-coronary commissure. The results also showed a general rise of the annular points in the positive z direction (direction superior to the computed plane) from the septal and anterior aspects of annulus toward the aortic valve for some datasets (particularly MRI1). This result suggests a saddle-shaped annulus.

Based on the analysis of the six datasets, the tricuspid valve annulus can be defined as a non-circular and non-planar shaped tissue structure, with a general relationship of minimum points along the septal and anterior aspects of the annulus and a rise up to a maximum height near the right coronary/non-coronary commissure of the aortic valve. These data suggest a distinct relationship between the tricuspid valve and the aortic valve, where the shape of the tricuspid valve near its interaction with the aortic valve may facilitate appropriate aortic valve function. Therefore, surgical repair procedures of the tricuspid valve should attempt to maintain this distinct relationship to both restore tricuspid valve function and maintain proper aortic valve function. In addition to this relationship, a consistent relationship was observed across the datasets for the TOK, indicating that the conductive tissue region of the heart near the tricuspid annulus makes up approximately 17% of the tricuspid annulus perimeter. This provides a reference point for appropriate termination of surgical repair of the tricuspid annulus along the septal annulus to avoid damage to the conductive tissue. General ranges for the preferred shape/design of a tricuspid valve annuloplasty device are defined in Table 5 below (based on averages of above data, plus or minus one standard deviation).

TABLE 5

General ranges for shape/design of a tricuspid valve annuloplasty device.

| | Range |
| --- | --- |
| 2D (Short Axis) Shape - Minor:Major Ratio | 0.75-0.96 |
| Percentage of Device Perimeter to Exclude Along Septal Aspect of Annulus to Avoid Conductive Tissue | 12-22% |
| Residual (Vertical) Offset Range of Maximum and Minimum Points from Computed Plane Through Device | 6.2-17.5 mm |
| Normal Offset of Maximum and Minimum Points from Computed Plane Through Device | −3 to +3 mm |
| Angular Position of Maximum Normal Offset With Respect to Axis Through Center Point of Device and Point on Device Closest to Right Coronary/Non-coronary Commissure | −100 to 0 degrees |

It is to be understood that while particular embodiments of the present inventive annuloplasty device have been illustrated for use in typical valve repair procedures, various modifications to shape, and arrangement of parts can be made as may be desirable for varying applications as may relate to valve sizes, disease states, or later developed techniques.

The present invention has now been described with reference to several embodiments thereof. The entire disclosure of any article, patent or patent application identified herein is hereby incorporated by reference. The foregoing detailed description has been given for clarity of understanding only. No unnecessary limitations are to be understood therefrom. It will be apparent to those skilled in the art that many changes can be made in the embodiments described without departing from the scope of the invention.

The invention claimed is:

1. An annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first end and second ends, the first end being at an end of the anterior portion, and the second end being at an end of the septal portion so that a gap is provided between the first and second ends; wherein the ring body is curvilinear, with substantially no flat portion along at least the anterior portion in any of three dimensions, forming a shape, and the ends are configured such that when the device is implanted, the first end will be located near the junction of the septal and anterior aspects of the annulus and the second end will be located near the septal aspect of the annulus with the AV node of such annulus within the gap an inward bow in the anterior portion such that when the device is implanted the bow will be locate near an aortic valve of the heart and the bow extends in the flow direction of the ring body and the blood flow direction of the tricuspid valve.

2. The annuloplasty device of claim 1, wherein the anterior portion comprises a curve extending in a superior direction, the posterior portion comprises a curve extending in the superior direction, the anterior portion curve extends farther in the superior direction than the posterior portion curve.

3. The annuloplasty device of claim 1, wherein the shape of the ring body mimics the shape of a native tricuspid valve annulus.

4. The annuloplasty device of claim 1, wherein the curvilinear shape includes varying slope between four slope minima.

5. The annuloplasty device of claim 1, wherein the ring body follows a path from first end to second end that contains at least two maximum and two minimum positions along the path.

6. The annuloplasty device of claim 1, wherein the ring body comprises a semi-rigid material.

7. The annuloplasty device of claim 1, wherein the ring body further comprises: a sheath; and, a stiffening element disposed within the sheath.

8. The annuloplasty device of claim 1, wherein upon implantation, the ends of the ring body avoid the AV node of the heart.

9. The annuloplasty device of claim 1, wherein upon implantation, the ends of the ring body and associated sutures avoid the Triangle of Koch of the heart.

10. The annuloplasty device of claim 1, wherein upon implantation, the device reduces the posterior aspect of the annulus.

11. The annuloplasty device of claim 1, wherein upon implantation, the device reduces the septal-lateral aspect of the annulus.

12. The annuloplasty device of claim 1, wherein relative to an upright orientation of the device in which the first end is spatially above the second end in a vertical dimension, an upward direction is spatially defined from the second end toward the first end, and an opposite, downward direction is defined from the first end toward the second end, and further wherein extension of the ring body from the first end includes a curve in the downward direction from a first maximum position to a first minimum position, a curve in the upward direction from the first minimum position to a second maximum position, a curve in the downward direction from the second maximum position to a second minimum position, and a projection in the upward direction from the second minimum position to the second end, wherein the first maximum position is above the second maximum position in the upward direction.

13. The annuloplasty device of claim 12, wherein the ring body curves in the upward direction from the first end to the first maximum position, and does not curve in the downward direction from the first end to the first maximum position.

14. The annuloplasty device of claim 13, wherein the ring body does not curve in the downward direction in the projection from the second minimum position to the second end.

15. An annuloplasty device for implantation adjacent an annulus of a tricuspid valve of a heart, the tricuspid valve having a flow orifice and a blood flow direction, and the annulus comprising anterior, posterior and septal aspects adjacent anterior, posterior and septal leaflets, respectively, of the tricuspid valve, the device comprising:

a ring body in the form of an arcuate band with a flow direction defined from a first side of the ring body to a second side of the ring body, the ring body comprising:
an anterior portion, a posterior portion and a septal portion shaped to conform to, and for implantation adjacent, the anterior, posterior and septal aspects of the annulus, respectively; and an inward bow in the anterior portion such that when the device is implanted the bow will be located near an aortic valve of the heart and the bow extends in the flow direction of the ring body and the blood flow direction of the tricuspid valve.

16. An annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first end and second ends, the first end being at an end of the anterior portion, and the second end being at an end of the septal portion so that a gap is provided between the first and second ends; wherein the ring body is curvilinear, with substantially no flat portion along at least the anterior portion in any of three dimensions, forming a shape, and the anterior portion comprises a curve extending in a superior direction, the posterior portion comprises a curve extending in the superior direction, the anterior portion curve extends farther in the superior direction than the posterior portion curve an inward bow in the anterior portion such that when the device is implanted the bow will be locate near an aortic valve of the heart and the bow extends in the flow direction of the ring body and the blood flow direction of the tricuspid valve.

* * * * *